US00PP32247P2

(12) United States Plant Patent
Van Swieten

(10) Patent No.: US PP32,247 P2
(45) Date of Patent: Sep. 29, 2020

(54) ***PHALAENOPSIS* ORCHID PLANT NAMED 'PHALGOCO'**

(50) Latin Name: ***Phalaenopsis* hybrid**
Varietal Denomination: PHALGOCO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,200

(22) Filed: Aug. 27, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

PUBLICATIONS

Upov Pluto Plant Variety Database Mar. 26, 2020, retrieved on Mar. 26, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALGOCO', particularly characterized by having reddish-purple flowers with very small white edges and dark red lips, 1 to 3 peduncles that are long and moderate, leaves that are oblong, and is propagated by meristem tissue culture, is disclosed.

3 Drawing Sheets

Genus and species: *Phalaenopsis* hybrid.
Variety denomination: 'PHALGOCO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGOCO'.

The new *Phalaenopsis* plant is a product of a planned breeding program conducted by the inventor in Bleiswijk, the Netherlands. The objective of this breeding program was to create a new *Phalaenopsis* plant having attractive reddish-purple flowers with very small white edges and dark red lips, suitable for potted plant production.

The new *Phalaenopsis* plant 'PHALGOCO' is a result of cross-pollination made by the inventor in October 2008 in Bleiswijk, the Netherlands, of the proprietary female, or seed parent, *Phalaenopsis* hybrid '14261-01' (unpatented) with the proprietary male, or pollen parent, *Phalaenopsis* hybrid '01-1569' (unpatented).

The new *Phalaenopsis* was selected by the inventor as a single plant within the progeny of the stated cross-pollination in a controlled greenhouse in Bleiswijk, the Netherlands, in January 2012. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 28, 2017, by Applicant who obtained the subject matter disclosed directly from the Inventor. 'PHALGOCO' has not been made publicly available or sold anywhere in the world prior to the effective filing date of this application with the exception of sales or disclosures made one year or less before the effective filing date of this claimed invention by Applicant who obtained 'PHALGOCO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGOCO' as a new and distinct variety of *Phalaenopsis* plant:

1) Reddish-purple flowers with very small white edges and dark red lips;
2) 1 to 3 peduncles;
3) Peduncle is long and moderately strong; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in March 2019. Colors in the photographs may differ from the color values cited in the detailed botanical description, which accurately describe the actual colors of the new variety.

DESCRIPTION OF THE NEW VARIETY

Figure 1:
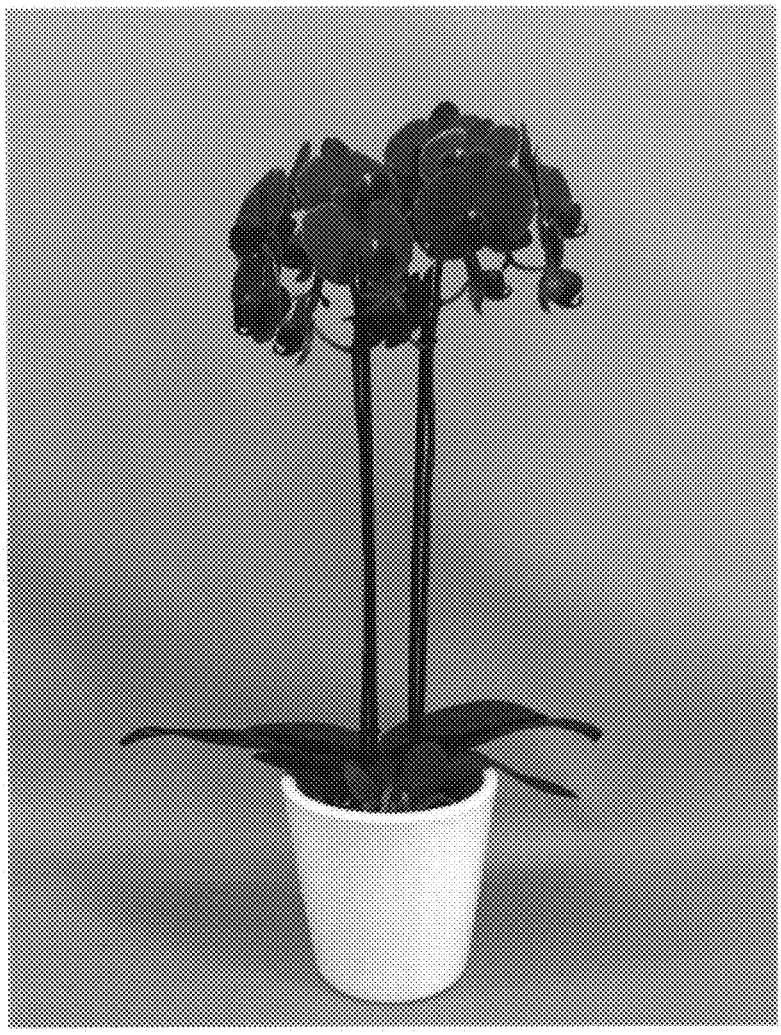
FIG. 1 shows the overall plant habit, including blooms and foliage of 'PHALGOCO'.
Figure 2:
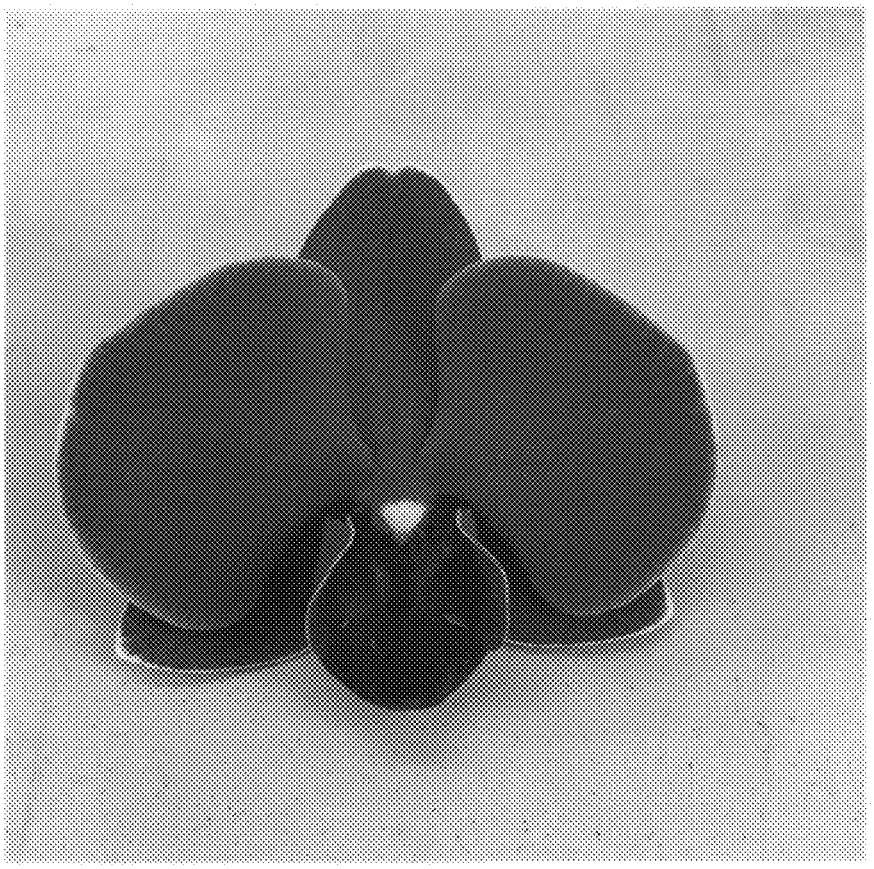
FIG. 2 shows a close-up of a flower of 'PHALGOCO'.
Figure 3:
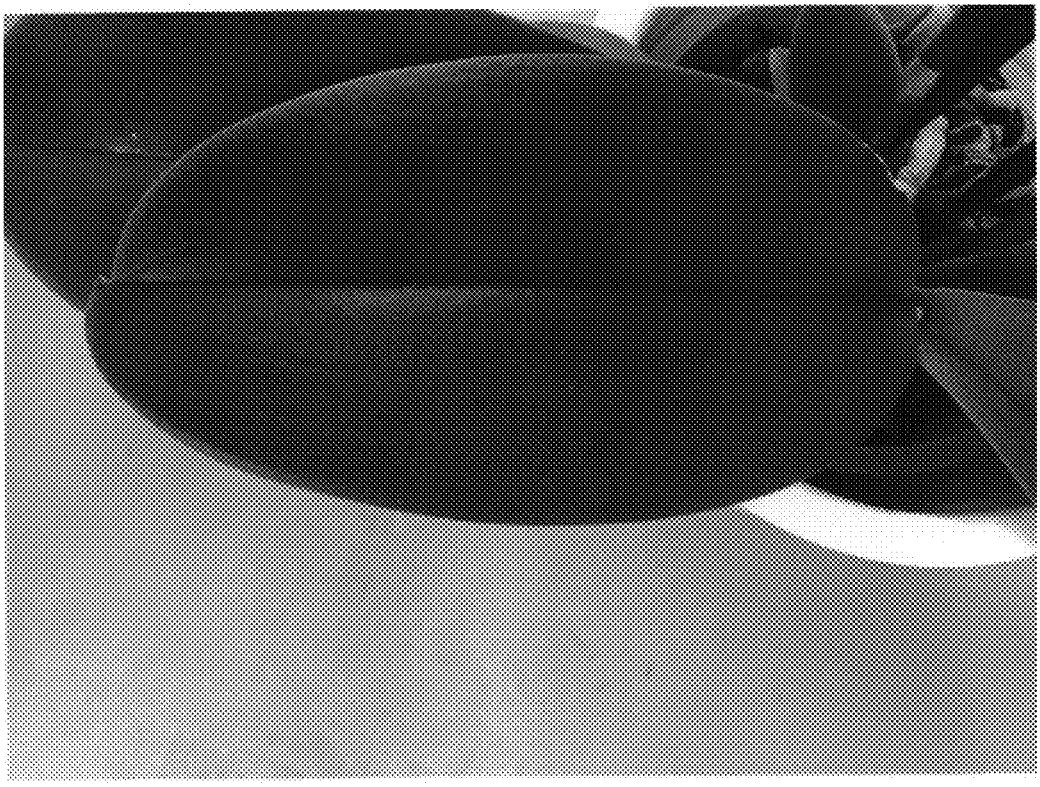
FIG. 3 shows an overhead view of the leaves of 'PHALGOCO'.

The following detailed description sets forth the distinctive characteristics of 'PHALGOCO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGOCO'.

Parentage:

*Female parent*.—*Phalaenopsis* cultivar '14261-01' (unpatented).

*Male parent*.—*Phalaenopsis* cultivar '01-1569' (unpatented).

Propagation:

*Type*.—Meristem tissue culture.

Roots:

*Root description*.—Greyed-green (between RHS 190B and 190C) colored roots with branching lateral roots having yellow-green (RHS 144C) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme inflorescence.

*Height (from soil level to top of inflorescence)*.—Approximately 50.0 cm to 55.0 cm.

*Width (measured from leaf tips)*.—About 37.0 cm to 39.0 cm.

*Vigor*.—Moderate.

Leaves:

*Mature leaves*.—Quantity per plant: 7 to 9 leaves are produced before flowering. Length (fully expanded): 16.0 cm to 20.0 cm. Width: 7.0 cm to 8.0 cm. Shape: Oblong. Base shape: Moderately elongated. Apex: Obtuse unequal. Leaf blade angle with the petiole (measured from the horizontal position): Between 5 degrees and 15 degrees. Leaf margin: Entire. Color: Upper surface: RHS 146A. Lower surface: RHS 146B. Spots (upper surface): None. Texture (both upper and lower surfaces): Rough. Thickness: 2.0 mm to 3.0 mm. Venation: Pattern: Parallel. Color of the midvein: Upper surface: RHS 147A. Lower surface: RHS 146C.

Peduncle:

*Quantity per plant*.—1 to 3.

*Number of flowers per peduncle*.—9 to 12.

*Length*.—50.0 cm to 55.0 cm.

*Diameter*.—4.0 mm to 5.0 mm.

*Strength*.—Strong.

*Aspect*.—Upright to slightly pendant.

*Texture*.—Smooth.

*Color*.—Yellow-green (RHS 146B) with a touch of brown (RHS N200A).

*Internode length*.—4.0 cm to 5.0 cm.

Inflorescence description:

*Appearance*.—Upright to slightly pendant, raceme inflorescence with bilaterally symmetrical flowers that open in succession beginning with the lowermost flower.

*Number of inflorescences*.—1 to 3.

*Inflorescence size*.—Height (from base to tip): 170.0 mm to 200.0 mm.

*Flowering time*.—First flowers can be expected 10 to 11 months after planting in a 12-cm pot.

*Flower*.—Height: 58.0 mm to 63.0 mm. Diameter: 73.0 mm to 78.0 mm. Depth of lip: 20.0 mm to 22.0 mm.

*Flower longevity*.—On the plant: 16 to 20 weeks.

*Fragrance*.—Absent.

*Flower bud*.—Average size: Large. Length: 19.0 mm to 21.0 mm. Width: 17.0 mm to 19.0 mm. Shape: Egg shaped. Color: Light yellow-green (RHS 145C) with a touch of red-purple (between RHS N79C and N79D).

*Petals*.—Arrangement: Open/free. Curvature at longitudinal axis: Straight. Shape: Semi-circular. Shape in cross section: Straight. Presence of any twisting: Absent. Apex: Rounded asymmetric. Margin: Entire. Intensity of undulation of the margin: Weak. Length (from base to tip): 33.0 mm to 35.0 mm. Width: 41.0 mm to 43.0 mm. Position of the broadest part of the petal: At the base. Color (when fully opened): Upper surface: Basic color: Reddish-purple (RHS N78A). Over color: Very small, very light purple edge (RHS 76B). Number of dots: Medium. Size of dots: Very small. Color of dots: RHS N78B to N78C. Lower surface: Basic color: Purplish-pink (RHS N78C). Over color: Reddish-purple base and edge (RHS N78B).

*Dorsal sepal*.—Curvature at longitudinal axis: Straight. Shape: Elliptic. Shape in cross section: Straight. Presence of any twisting: Absent. Apex: Emarginated symmetric. Margin: Entire. Intensity of undulation of the margin: Absent. Length (from base to tip): 34.0 mm to 36.0 mm. Width: 25.0 mm to 27.0 mm. Color (when fully opened): Upper surface:

Basic color: Reddish-purple (RHS N78A). Over color: Purplish-red (RHS 71A) in the middle and a very small, very light purple edge (RHS 76B). Number of dots: Many. Size of dots: Very small. Color of dots: RHS N78C. Lower surface: Basic color: Reddish-purple (RHS N78B). Over color: Light yellow-green (RHS 196C) in the middle.

*Lateral sepals*.—Shape: Ovate. Apex: Obtuse asymmetric. Margin: Entire. Length (from base to tip): 35.0 mm to 37.0 mm. Width: 23.0 mm to 25.0 mm. Color (when fully opened): Upper surface: Basic color: Reddish-purple (RHS N78A). Over color: Light yellow-green (RHS 145D) at the base; dotted (RHS 59A). Lower surface: Basic color: Purplish-pink (RHS N78C). Over color: Light yellow-green (RHS 145B) at the base and reddish-purple edge (RHS N78B).

*Labellum* (*lip*).—Whiskers: Present. Length of whiskers: 7.0 mm to 9.0 mm. Color of whiskers: Dark red (RHS 187A). Pubescence on the lip: Absent.

*Lateral lobe*.—Shape: Type V (as described in the International Union for the Protection of New Varieties of Plants (UPOV) Test Guidelines for *Phalaenopsis*); spatulate. Curvature: Medium. Margin: Undulated. Length: 15.0 mm to 19.0 mm. Width: 13.0 mm to 15.0 mm. Color: Slightly brown (RHS 172A) at the base; dark red (RHS 187B); slightly reddish-purple (RHS N78A) toward the margin. Number of stripes and netting: None. Fusion of the lateral lobes to the apical lobe: None.

*Apical lobe*.—Shape: Trullate. Margin: Entire. Length: 17.0 mm to 19.0 mm. Width: 19.0 mm to 21.0 mm. Color: Dark red (RHS 59A). Number of spots, stripes, and netting: None.

*Callus*.—Average size: Medium. Height: 6.0 mm to 7.0 mm. Length: 5.0 mm to 6.0 mm. Width: 3.0 mm to 4.0 mm. Color: Dark reddish-orange (RHS 178B) with a touch of slightly yellow (RHS 8A).

Reproductive organs:

*Column*.—Length: 8.0 mm to 10.0 mm. Diameter: 5.1 mm to 5.4 mm. Color: Reddish-purple (RHS N78A).

*Pollinia*.—Quantity: 2. Diameter: 0.9 mm to 1.1 mm. Color: Orange (RHS 24A).

*Ovary*.—Length: 8.0 mm to 10.0 mm. Diameter: 2.2 mm to 2.4 mm. Color: Light yellow-green (RHS 145D) with a touch of very light purple (RHS 76C) toward the flower.

*Pedicel*.—Length: 30.0 mm to 32.0 mm. Diameter: 2.6 mm to 2.8 mm. Color: Yellow-green (between RHS 145A and 145B) at the base; light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGOCO' differs from female parent plant '14261-01' (unpatented) in that 'PHALGOCO' has flowers with a basic color of reddish-purple, whereas '14261-01' has flowers with a basic color of very light purple. Additionally, 'PHALGOCO' has smaller flowers and shorter whiskers than '14261-01'.

The male parent plant of 'PHALGOCO', cultivar '01-1569' (unpatented), is no longer in existence, therefore a meaningful comparison cannot be made.

'PHALGOCO' is most similar to the commercial *Phalaenopsis* plants named 'PHALDANBO' (U.S. Plant Pat. No. 25,930) and 'PHALDUKAI' (U.S. Plant Pat. No. 28,157). 'PHALGOCO' differs from the commercial variety 'PHALDANBO' in that 'PHALGOCO' has smaller flowers, shorter leaves, shorter whiskers, and narrower dorsal sepals than 'PHALDANBO'.

'PHALGOCO' differs from the commercial variety 'PHALDUKAI' in that 'PHALGOCO' has smaller flowers, shorter leaves, shorter whiskers, narrower petals, and narrower dorsal sepals than 'PHALDUKAI'.

I claim:

1. A new and distinct variety of *Phalaenopsis* plant named 'PHALGOCO', substantially as described and illustrated herein.

* * * * *